(12) United States Patent
Roorda et al.

(10) Patent No.: US 9,011,928 B2
(45) Date of Patent: Apr. 21, 2015

(54) COMPOSITIONS FOR ACHIEVING A THERAPEUTIC EFFECT IN AN ANATOMICAL STRUCTURE

(71) Applicant: Abbott Cardiovascular Systems Inc., Santa Clara, CA (US)

(72) Inventors: Wouter E. Roorda, Palo Alto, CA (US); Stephen D. Pacetti, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 14/074,201

(22) Filed: Nov. 7, 2013

(65) Prior Publication Data

US 2014/0065093 A1    Mar. 6, 2014

Related U.S. Application Data

(60) Division of application No. 13/244,294, filed on Sep. 24, 2011, now Pat. No. 8,632,820, which is a continuation of application No. 12/198,749, filed on Aug. 26, 2008, now Pat. No. 8,057,824, which is a division of application No. 11/015,943, filed on Dec. 17, 2004, now abandoned, which is a division of application No. 09/781,599, filed on Feb. 12, 2001, now Pat. No. 7,008,642.

(51) Int. Cl.
| | |
|---|---|
| *A61K 47/26* | (2006.01) |
| *A61K 47/36* | (2006.01) |
| *A61K 9/14* | (2006.01) |
| *A61K 9/16* | (2006.01) |
| *A61K 31/727* | (2006.01) |
| *A61K 31/573* | (2006.01) |
| *A61K 38/18* | (2006.01) |
| *A61K 48/00* | (2006.01) |

(52) U.S. Cl.
CPC .................. *A61K 9/14* (2013.01); *A61K 9/1617* (2013.01); *A61K 9/1647* (2013.01); *A61K 9/1658* (2013.01); *A61K 31/727* (2013.01); *A61K 47/26* (2013.01); *A61K 47/36* (2013.01); *A61K 31/573* (2013.01); *A61K 38/1825* (2013.01); *A61K 9/1694* (2013.01); *A61K 48/00* (2013.01)

(58) Field of Classification Search
None
See application file for complete search history.

(56) References Cited

U.S. PATENT DOCUMENTS

| | | | |
|---|---|---|---|
| 3,932,434 A | 1/1976 | Paget et al. | |
| 4,675,189 A | 6/1987 | Kent et al. | |
| 4,733,665 A | 3/1988 | Palmaz | |
| 4,800,882 A | 1/1989 | Gianturco | |
| 4,886,062 A | 12/1989 | Wiktor | |
| 5,028,263 A | 7/1991 | Burdick | |
| 5,879,713 A * | 3/1999 | Roth et al. | 424/489 |
| 5,993,374 A | 11/1999 | Kick | |
| RE37,410 E | 10/2001 | Brem et al. | |
| 6,599,516 B1 | 7/2003 | Knaack | |

FOREIGN PATENT DOCUMENTS

| | | |
|---|---|---|
| JP | 09-165327 | 6/1997 |
| JP | 09-165328 | 6/1997 |

OTHER PUBLICATIONS

Alginic acid, *Wikipedia*, http://en.wikipedia.org.wiki/Alginic_acid, printed Jun. 6, 2010, 4 pages.
Croscarmellose sodium, http://www.nbent.com/crosscarmellose.htm, printed Jul. 23, 2007, 2 pages.
Hygroscopy, *Wikipedia*, http://en.wikipedia.org.wiki/Hygroscopic, printed Jul. 23, 2007, 2 pages.
Poly vinyl pyrrolidone, *Wikipedia*, http://en.wikipedia.org.wiki/Poly_vinyl_pyrrolidone, printed Jul. 23, 2007, 3 pages.
Sodium alginate, *FAO Corporate Document Repository*, http://www.fao.org/docrep/w6355e/w6355e0x.htm, printed Jun. 6, 2010, 2 pages.
English Translation for JP 09-165328 cited above.
Alexandridis et al., Poly(ethylene oxide)—poly(propylene oxide)—poly(ethylene oxide) block copolymer surfactants in aqueous solutions and at interfaces: thermodynamics, structure, dynamics, and modeling (1995) *Colloids and Surfaces A: Physicochemical and Engineering Aspects* 96:1-46.
Span® 80 nonionic surfactant I Sigma-Aldrich, http://www.sigmaaldrich.com/catalog/product/sigma/s6760?lang=en&region=US, Oct. 30, 2014, 1 page.
The Merck Index Online, Polysorbates, https://ez03.infotrieve.com:2548/Merck-Index/monograph/print/mono1500007703/polyso . . . , Nov. 11, 2014, 1 page.
Tween 85, http://www.chemblink.com/products/9005-70-3.htm, Oct. 31, 2014, 2 pages.
Tween®, http://www4.mpbio.com/ecom/docs/proddata.nsf/(webtds2)/103168, Oct. 31, 2014, 4 pages.

* cited by examiner

*Primary Examiner* — Mina Haghighatian
*Assistant Examiner* — Luke Karpinski
(74) *Attorney, Agent, or Firm* — Squire Patton Boggs (US) LLP

(57) ABSTRACT

Compositions and methods of using the compositions are provided for forming an embolus within a region of an anatomical lumen for a transitory period in order to achieve a therapeutic effect.

14 Claims, 6 Drawing Sheets

COMPOSITIONS FOR ACHIEVING A THERAPEUTIC EFFECT IN AN ANATOMICAL STRUCTURE

CROSS-REFERENCE TO RELATED APPLICATIONS

This application is a divisional application of U.S. application Ser. No. 13/244,294, filed on Sep. 24, 2011, published on Feb. 9, 2012, as U.S. Patent Application Publication No. 2012-0035107 A1, and subsequently issued as U.S. Pat. No. 8,632,820 B2 on Jan. 21, 2014, which is a continuation of U.S. application Ser. No. 12/198,749 filed on Aug. 26, 2008, and subsequently issued as U.S. Pat. No. 8,057,824 on Nov. 15, 2011, which is a division of U.S. application Ser. No. 11/015,943 filed on Dec. 17, 2004, and published as U.S. Pat App Pub No. 2005-0142202 A1 on Jun. 30, 2005, which is a division of U.S. application Ser. No. 09/781,599 filed on Feb. 12, 2001, and subsequently issued as U.S. Pat. No. 7,008,642 on Mar. 7, 2006; each of which is hereby incorporated by reference herein in its entirety. Incorporation by reference of U.S. application Ser. No. 13/244,294 includes drawings.

BACKGROUND OF THE INVENTION

1. Field of the Invention

The present invention relates generally to compositions that induce a therapeutic response within an anatomical structure. More specifically, the invention is directed to compositions of matter for achieving a therapeutic effect in a localized region of a mammalian lumen or network of lumens, such as within the vascular system. Moreover, the invention is directed to methods of using the compositions of matter for treatment of the targeted area.

2. Description of the Related Art

The cardiovascular system is characterized by extensive branching of blood vessels. The three major types of blood vessels are arteries, veins, and capillaries. Arteries and veins are distinguished by the direction of blood flow within them rather than by the quality of the blood they carry. Most arteries, but not all, carry oxygenated blood, and most veins, but not all, carry deoxygenated blood. All arteries carry blood from the heart to the capillaries, and all veins return blood back to the heart from the capillaries. While arteries and veins act as conduits for the flow of blood, capillaries come into intimate contact with tissue cells to directly serve cellular needs. Exchange of oxygen and carbon dioxide between the blood and tissue cells occurs primarily through the thin walls of the capillaries.

FIG. 1 illustrates the extensive branching of blood vessels in an anatomical structure 10 within the mammalian cardiovascular system. As the heart alternately contracts and relaxes, blood is forced in a direction 12 into successively smaller arterial vessels.

The three types of arterial vessels include elastic arteries 14, muscular arteries 16, and arterioles 18. Elastic arteries 14, such as the aorta and major aortic branches, are the large, thick walled arteries near to the heart. Of the three types of arterial vessels, elastic arteries 14 are the largest in diameter and the most elastic. Elastic arteries 14 are sometimes referred to as conducting arteries because the large diameters of the vessels provide little resistance against the flow of blood. Muscular arteries 16, also referred to as distributing arteries, are the second type of arterial vessel. Muscular arteries 16 extend from elastic arteries 14 to deliver blood to specific organs. The smallest of the arterial vessels are arterioles 18. Arterioles 18 typically have a lumen diameter smaller than 0.3 mm. The smallest arterioles 18 are little more than a single layer of smooth muscle cells spiraling around the endothelial lining.

From arteriole 18, blood flows in direction 12 to capillaries 20. Capillaries 20 form networks of microscopic vessels that infiltrate tissues. It is across the thin walls of capillaries 20 that blood releases oxygen and receives the carbon dioxide produced by cellular respiration. The microscopic capillaries 20 are the smallest blood vessels. In some cases, one cell forms the entire circumference of the capillary wall.

Deoxygenated blood is carried in direction 12 from the bed of capillaries 20 toward the heart by venous vessels. En route, the venous vessels increase in diameter and their walls gradually thicken in progression from venules 22 to small veins 24 to larger veins 26. Occlusion of venous vessels rarely blocks blood flow. The vast union of branches among the venous vessels provides alternative pathways for the flow of blood. Thus, if a region of a venous vessel becomes occluded, the anastomotic formation of the vessels allows for the proper circulation of blood back to the heart.

Occlusion of arterial vessels, however, typically reduces or blocks blood flow. During the course of atherosclerosis, for example, growths called plaques develop on the inner walls of the arteries and narrow the bore of the vessels. An embolis, or a moving clot, is more likely to become trapped in a vessel that has been narrowed by plaques. Further, plaques are common sites of thrombus formation. Together, these events increase the risk of heart attacks and strokes.

Traditionally, critically stenosed atherosclerotic vessels have been treated with bypass surgery in which veins removed from the legs, or small arteries removed from the thoracic cavity, are implanted in the affected area to provide alternate routes of blood circulation. More recently, intravascular devices, such as stents, have been used to treat diseased blood vessels.

Stents are scaffoldings, usually cylindrical or tubular in shape, which function to physically hold open and, if desired, to expand the wall of the vessel. Typically stents are capable of being compressed, so that they may be inserted through small cavities via catheters, and then expanded to a larger diameter once they are at the desired location.

Although stents are significant innovations in the treatment of occluded vessels, a common problem with usage of stents is restenosis. Restenosis of the artery commonly develops over several months after a therapeutic procedure, which may require another angioplasty procedure or a surgical by-pass operation. Restenosis is thought to involve the body's natural healing process. Angioplasty or other vascular procedures injure the vessel walls, removing the vascular endothelium, disturbing the tunica intima, and causing the death of medial smooth muscle cells. Excessive neoinitimal tissue formation, characterized by smooth muscle cell migration and proliferation to the intima, follows the injury. Proliferation and migration of smooth muscle cells (SMC) from the media layer to the intima cause an excessive production of extra cellular matrices (ECM), which is believed to be one of the leading contributors to the development of restenosis. The extensive thickening of the tissues narrows the lumen of the blood vessel, constricting or blocking blood flow through the vessel.

Thus, although stents are significant innovations in the treatment of occluded vessels, there remains a need for administering therapeutic substances to the treatment site. To provide an efficacious concentration to the treatment site, systemic administration of the therapeutic substance often produces adverse or toxic side effects for the patient. Local delivery is a highly suitable method of treatment, in that smaller levels of therapeutic substances, as compared to systemic dosages, are concentrated at a specific site. Local delivery produces fewer side effects and achieves more effective results.

One commonly applied technique for the local delivery of a therapeutic substance employs a porous balloon attached to a distal end of a catheter assembly. The expansion of the balloon, which in effect results in the dilation of the occluded region, is accomplished by injecting a therapeutic substance into the balloon. The use of a therapeutic substance as an expansion fluid additionally functions as a medicament for the diseased region, as the therapeutic substance is discharged from the porous balloon during and subsequent to the expansion therapy. A shortcoming associated with this procedure is that the therapeutic substance may be carried off in the patient's blood stream as it is being discharged from the balloon, which results in an ineffective treatment of the target site and adverse exposure of the substance to healthy tissues.

Another technique for the local delivery of a therapeutic substance employs a medicated implantable device, such as a stent. A stent coated with a polymeric material, which is impregnated with a therapeutic substance, can be deployed at a selected site of treatment. The polymeric carrier allows for a sustained delivery of the therapeutic substance. An obstacle associated with the use of medicated stents is the limited ability of the stents to access the smaller vessels within the mammalian cardiovascular system. Another obstacle associated with the use of a medicated stent is that the therapeutic substance is primarily delivered to the vessel wall which is in direct contact with the stent. Thus, delivery of the therapeutic substance to other localized areas of the vessel or to localized areas of tissue located adjacent to the vessel is not easily facilitated.

Another technique for the local delivery of a therapeutic substance is disclosed in U.S. Pat. No. 5,879,713 to Roth et al. Roth et al. teaches the administration of microparticles that include a polymeric carrier and biologically active molecules. The microparticles selectively lodge at a targeted site within the vascular system for a sufficient amount of time to permit controlled release of a therapeutically effective amount of the biologically active molecules. Roth et al. further teaches that suitable polymer compositions preferably have intrinsic and controllable biodegradability, so that they persist for about a week to about six months. A shortcoming of Roth et al., however, is that an embolization period of one week may be too long for some vessels, such as those in the brain or in the coronary system, and may thus lead to death in the tissue supplied by such vessels.

SUMMARY

In accordance with the present invention, a method of achieving a therapeutic effect is provided. The method includes providing a particle containing a therapeutic substance to an anatomical structure having a lumen such that the particle embolizes within the lumen for a transitory period of less than one week. The therapeutic substance is released from the particle, causing a therapeutic effect.

Another method of achieving a therapeutic effect is also provided. The method includes providing a particle to an anatomical structure having a lumen such that the particle embolizes within the lumen for a transitory period. The transitory period of embolization causes a brief period of reduced blood flow through the lumen that induces a therapeutic bodily response.

A composition for achieving a therapeutic effect in an anatomical structure having a lumen is also provided. The composition includes a particle suitable for introduction into an anatomical structure. The particle contains a therapeutic substance and is capable of reducing in size. The particle is capable of embolizing within the lumen for a transitory period of less than one week. The therapeutic substance is released from the particle for the treatment of a patient.

Also provided is another composition for achieving a therapeutic effect in an anatomical structure having a lumen. The composition includes a particle suitable for introduction into an anatomical structure and capable of reducing in size. The particle is capable of embolizing within the lumen for a transitory period, causing a brief period of reduced blood flow which induces a therapeutic bodily response.

Also provided is a method of achieving a therapeutic effect within an anatomical structure having a first region as well as a second region located downstream of the first region and having a smaller cross-sectional diameter than the first region. The method includes the act of providing a particle having a first size in which the particle is not capable of passing from the first region into the second region. The particle is capable of reducing in size. The method also includes the act of delivering the particle having the first size to the first region of the anatomical structure. The particle subsequently reduces from the first size to a smaller second size as the particle travels through the anatomical structure, allowing the particle to pass into the second region, and a therapeutic effect is achieved.

In some embodiments of the method, the particle includes a therapeutic substance that is released from the particle. In such embodiments, the therapeutic effect results from the therapeutic substance.

In alternative embodiments, during the act of traveling through the anatomical structure and prior to the act of reducing to the second size, the particle reaches a diameter of the anatomical structure through which the particle cannot pass and at which the particle is constrained for a transitory period until the particle reduces to the second size. In some such embodiments in which the anatomical structure is within a mammalian cardiovascular system, a brief period of reduced blood flow is caused during the transitory period. The therapeutic effect is a therapeutic bodily response induced by the brief period of reduced blood flow. In other such embodiments in which the particle includes a therapeutic substance and in which the transitory period is less than one week, the therapeutic substance is released from the particle. The resulting therapeutic effect is due to the therapeutic substance.

These and other aspects of the present invention may be better appreciated in view of the detailed description and drawings of the exemplary embodiments.

DETAILED DESCRIPTION

The present invention discloses novel compositions and methods that allow delivery of a therapeutic substance to a diseased region in the mammalian anatomy without significant loss of the therapeutic substance caused by the downstream flow of a fluid, such as blood. The invention provides compositions that are capable of treating multiple regions of a particular lumen, or of a particular network of lumens, simultaneously. The compositions and methods have a therapeutic effect, via reduction in blood flow to a lumen or via sustained release of a therapeutic substance, in anatomical structures that may not have suitable diameters for other techniques of treatment.

Composition of Matter

Figure 1:
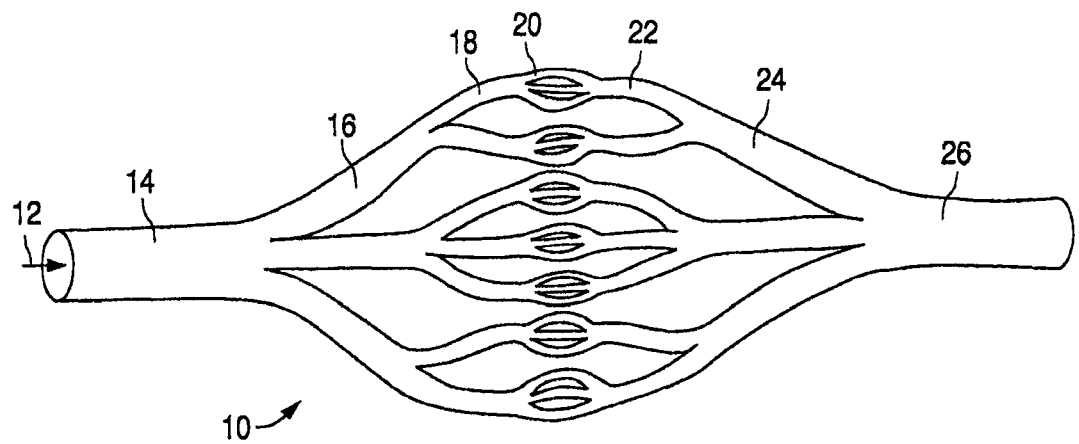
FIG. 1 is an example of a heavily-branched network of blood vessels within the mammalian cardiovascular system.
Figure 2:
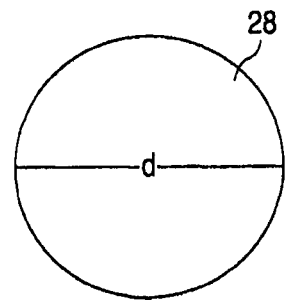
FIG. 2 illustrates a particle capable of embolizing within a lumen for a transient period of time.

Referring to FIG. 2, a particle 28 is disclosed that is capable of being deposited in a passageway through which a substance, such as a body fluid, is transported. Particle 28 can embolize within a lumen for a transitory period of time to induce a therapeutic response. The therapeutic response can be induced, for example, by the reduction in flow of a substance, such as blood, through the passageway or by the sustained delivery of a therapeutic substance or a combination of therapeutic substances.

Particle 28 can have any suitable initial size such that it is capable of being lodged within a region of a passageway upon delivery. A suitable range for an initial diameter d of particle 28 is from about 5 microns to about 100 microns. The actual diameter d depends on the procedure for which particle 28 is used and the size of the lumen in which particle 28 is to be inserted.

Typically, the material from which particle 28 is made is most suitably a biocompatible, particularly hemocompatible, material that is non-toxic, non-inflammatory, chemically inert, and substantially non-immunogenic in the amounts employed. Suitable materials from which particle 28 may be made include, but are not limited to, waxes and polymeric materials. Examples of such waxes include partially hydrogenated vegetable oils, triglycerides, beeswax, saturated fatty acids, fatty acid esters, and phospholipids.

Suitable polymeric materials include, but are not limited to, bioabsorbable polymers, biomolecules, biodegradable inorganics, and biostable polymers. A bioabsorbable polymer breaks down in the body and is not present sufficiently long after delivery to cause an adverse local response. Bioabsorbable polymers are gradually absorbed or eliminated by the body by hydrolysis, metabolic process, bulk, or surface erosion. Examples of bioabsorbable materials include, but are not limited to, polycaprolactone (PCL), poly-D, L-lactic acid (DL-PLA), poly-L-lactic acid (L-PLA), poly(lactide-co-glycolide), poly(hydroxybutyrate), poly(hydroxybutyrate-co-valerate), polyorthoesters, polyanhydrides, poly(glycolic acid), poly(glycolic acid-co-trimethylene carbonate), polyphosphoesters, polyphosphoester urethane, poly (amino acids), cyanoacrylates, poly(trimethylene carbonate), poly (iminocarbonate), copoly(ether-esters), polyalkylene oxalates, polyphosphazenes, polyiminocarbonates, and aliphatic polycarbonates. Biomolecules such as dextran, hyaluronic acid, chondroitin sulfate, glycosaminoglycans, elastin, albumin, heparin, fibrin, fibrinogen, cellulose, starch, and collagen are typically also suitable. Examples of suitable biodegradable inorganics include, but are not limited to, hydroxyapatite, dahlite, brushite, calcium sulphate, octacalcium phosphate, amorphous calcium phosphate, and beta-tricalcium phosphate. A biostable polymer does not break down in the body, and thus a biostable polymer is present in the body for a substantial amount of time after delivery unless some modification is made to allow the polymer to break down. Examples of biostable polymers include, but are not limited to, Parylene®, Parvlast®, polyurethane (for example, segmented polyurethanes such as Biospan®), polyethylene, polyethylene terephthalate, ethylene vinyl acetate, silicone, and polyethylene oxide.

In addition, particle 28 may be made of more than one material. In one embodiment, particle 28 includes a mixture of at least two different materials, each of which reduces in size in the lumen network of anatomical structure 10 at a different rate. In another embodiment, particle 28 includes a first material and a second material that covers at least a portion of the first material. In such an embodiment, each material reduces in size in the lumen network of anatomical structure 10 at a different rate.

In some embodiments, particle 28 contains a therapeutic substance that is carried by the material of which particle 28 is made. The carrier substance and the therapeutic substance within a single particle should be mutually compatible, such that the characteristics, effectiveness, and physical structure of the therapeutic substance and the carrier substance are not adversely altered. In addition, more than one therapeutic substance may be contained in a single particle 28. The number, type, and concentration of therapeutic substances within particle 28 are treatment-specific.

Therapeutic substances or agents may include, but are not limited to, antineoplastic, antimitotic, anti-inflammatory, antiplatelet, anticoagulant, anti fibrin, antithrombin, antiproliferative, antibiotic, antioxidant, antiallergic, antiangiogenic, angiogenic, and arteriogenic substances as well as combinations thereof. Examples of such antineoplastics and/or antimitotics include paclitaxel (e.g., TAXOL® by Bristol-Myers Squibb Co., Stamford, Conn.), docetaxel (e.g., TAXOTERE® from Aventis S. A., Frankfurt, Germany) methotrexate, azathioprine, vincristine, vinblastine, fluorouracil, doxorubicin hydrochloride (e.g., ADRIAMYCIN® from Pharmacia & Upjohn, Peapack N.J.), and mitomycin (e.g., MUTAMYCIN® from Bristol-Myers Squibb Co., Stamford, Conn.) Examples of such suitable anti-inflammatories include glucocorticoids such as dexamethasone, methylprednisolone, hydrocortisone and betamethasone, superpotent glucocorticoids such as clobetasol, halobetasol, and diflucortolone, and non-steroidal anti-inflammatories such as aspirin, indomethacin and ibuprofen. Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as ANGIOMAX™ (Biogen, Inc., Cambridge, Mass.). Examples of such cytostatic or antiproliferative agents include actinomycin D as well as derivatives and analogs thereof (manufactured by Sigma-Aldrich, Milwaukee, Wis.; or COSMEGEN™ available from Merck & Co., Inc., Whitehouse Station, N.J.), angiopeptin, angiotensin converting enzyme inhibitors such as captopril (e.g., CAPOTEN® and CAPOZIDE® from Bristol-Myers Squibb Co., Stamford, Conn.), cilazapril or lisinopril (e.g., PRINIVIL® and PRINZIDE® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name MEVACOR® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Examples of antiangiogenic agents include thalidomide and angiostatin. Examples of angiogenic agents include vascular endothelial cell growth factor (VEGF) and fibroblast growth factor (FGF). Examples of arteriogenic agents include histimine, MCP-1, lipo-polysaccharide, and β-FGF. Other therapeutic substances or agents that may be used include alpha-interferon, genetically engineered epithelial cells, and dexamethasone. While the preventative and treatment properties of the foregoing therapeutic substances or agents are well-known to those having ordinary skill in the art, the substances or agents are provided by way of example and are not meant to be limiting. Other therapeutic substances are equally applicable for use with the disclosed methods and compositions.

Preparation of Particles

Numerous methods are known to those having ordinary skill in the art for preparing particles 28, with or without a therapeutic substance. Such methods include, but are not limited to, spray drying, supercritical spray drying, emulsion techniques, grinding, and microencapsulation.

Spray drying is a versatile technique, as the primary requirement is the use of a fairly volatile solvent. Suitable solvent volatilities range from that of methylene chloride to that of water. In this particle 28 preparation method, the material of which particle 28 is to be made is dissolved in a volatile solvent to form a solution. In embodiments in which particle 28 also contains a therapeutic substance, the therapeutic substance is suspended or co-dissolved in the solution. In such embodiments, particular care should be taken to ensure that the therapeutic substance is stable at the spray drying temperature and able to withstand exposure to liquid-gas interfaces. The solution is then spray-dried, a technique that is well known to one of ordinary skill in the art. Any suitable spray drier may be used with any suitable parameters. Typical process parameters for a mini-spray-drier, such as Büchi™, include an inlet temperature of −24° C., an outlet temperature of 13-15° C., a pump setting of 10 mL/minute, a spray flow of 600 N1/hr, and a nozzle diameter of 0.5 mm. The size of resulting particles 28 is dependent on the actual percent solids and spray drier parameters employed.

Another method of particle 28 preparation is supercritical spray drying. Several variations of supercritical spray drying techniques are known. In one such variation, a solution containing a solvent and the material of which particle 28 is to be made, with or without a therapeutic substance, is sprayed into a supercritical solvent, such as carbon dioxide. The supercritical solvent effectively extracts the solvent used to dissolve the material of which particle 28 will be made. This technique may be carried out at a temperature as low as 32° C. In another variation of supercritical spray drying, the material of which particle 28 is to be made, with or without a therapeutic substance, is dissolved in the supercritical solvent. The resulting solution is spray-dried, and the supercritical solvent rapidly flashes off at room temperature to yield particles 28.

Particles 28 may also be prepared via a number of emulsion techniques. One such technique involves the preparation of an oil-in-water emulsion. The material of which particle 28 will be made, with or without a therapeutic substance, is dissolved in an organic solvent, usually with an emulsifier. The oil phase is dispersed into water using ultrasonication, mechanical agitation, or a microfluidizer. The organic solvent is then removed by evaporation, and particles 28 are collected and washed. The size of particles 28 is primarily dependent on the percent solids of the oil phase, the shear rate, and stability of the dispersed phase. This technique also allows preparation of stable aqueous latexes of water insoluble particles 28.

Water-in-oil emulsions, which are known to those having ordinary skill in the art, tend to be less stable than the above-described oil-in-water emulsions. However, a stable solution may be spray-dried to yield particles 28 in the form of microcapsules containing an aqueous phase.

A double emulsion technique, such as a water-in oil-in-water emulsion, is typically used to produce particles 28 in the form of microcapsules containing a therapeutic substance. The therapeutic substance is dissolved into the water phase and the material of which particle 28 is made is dissolved into the oil phase. Emulsification is accomplished by adding the water phase to the oil phase. The solution is immediately added to another aqueous phase with additional emulsification. The solvent is removed, typically by evaporation. The water may be left in the capsule or removed by evaporation or lyophilization. Unlike the above-described oil-in-water system, this water-in-oil-in-water system allows particles 28 to be formed from water soluble materials.

Still other methods of making particles 28 include methods in which a carrier substance and a therapeutic substance are combined by conventional solvent-processing or melt-processing methods known to those having ordinary skill in the art. Monolithic pieces are then cast or fabricated, and fine particles 28 are made by grinding, milling or pulverizing such pieces. Particular care should be taken to control the processing temperature employed in embodiments in which the therapeutic substance is temperature-sensitive.

Particles 28 may also be prepared using microencapsulation techniques. Various methods for microencapsulation are known by persons having ordinary skill in the art, including methods of making various microparticles having water-soluble compounds within them. A person of ordinary skill in the art will appreciate that a peptide may be substituted with any rapidly swelling super-disintegrant. The appropriate amount of such super-disintegrant may be from about 0.1% to about 60%, or more particularly from about 10% to about 15%, by volume in the final microparticle.

Control of Particle Size Reduction Rate

Regardless of how particle 28 is made, particle 28 must ultimately be capable of size reduction. Not only must particle 28 be able to reduce from a first size to a smaller second size, particle 28 should also be capable of doing so at a controlled rate such that particle 28 embolizes within the lumen for a transient period of time. For example, particle 28 should embolize within the lumen long enough to induce a therapeutic effect but not so long as to cause cell death in distal tissues. Further, in embodiments in which particle 28 contains a therapeutic substance, the transitory period of embolization preferably be less than one week. Several mechanisms may be employed to control the rate at which particle 28 reduces in size and thereby control the amount of time for which particle 28 will embolize within a lumen.

a. Rapid Hydrolysis

Hydrolysis is the mechanism by which many bioerodable polymers, including polyesters, polyanhydrides, and polyphosphazenes, erode. Most such materials erode over a period of days to months and, as such, are too long-lived for use in accordance with some embodiments in the present disclosure.

Yet selection of particles 28 made from certain hydrophilic polyanhydrides can yield particles 28 capable of the relatively rapid erosion rates suitable for use in the present technique. Of particular applicability are those hydrophilic polyanhydrides based on hydrophilic diacids. Such hydrophilic diacids include, but are not limited to, fumaric acid, maleic acid, succinic acid, and di-basic amino acids.

b. Controlled Dissolution

In some embodiments, a hydrophobic solid may be selected as the material from which to make particle 28 to ensure a controlled dissolution rate of particle 28. Such hydrophobic solids include, but are not limited to, cholesterol, solid triglycerides, and hydrophobic proteins. Other potential compounds from which particle 28 may be made include surfactants such as those from the SPAN®, TWEEN®, and PLURONIC® family of surfactants. SPAN and TWEEN are registered trademarks of ICI Americas Inc. of Wilmington, Del. and PLURONIC is a trademark of BASF Corp. of Parsippany, N.J. SPAN® surfactants are sorbitan esters. Commercially available SPAN® surfactants include SPAN® 20 (Sorbitan monolaurate), SPAN® 40 (Sorbitan monoplamitate), SPAN® 60 (Sorbitan monostearate), SPAN® 80 (Sorbitan monooleate), SPAN® 83 (Sorbitan sesquioleate), SPAN® 85 (Sorbitan trioleate), and SPAN® 120 (Sorbitan isostearate). TWEEN® surfactants are polyethoxylated sorbitan esters. Commercially available TWEEN® surfactants include TWEEN® 20 (PEG 20 Sorbitan monolaurate), TWEEN® 21 (PEG 4 Sorbitan monolaurate), TWEEN® 40 (PEG 20 Sorbitan monopalmitate), TWEEN® 60 (PEG 20 Sorbitan monostearate), TWEEN® 61 (PEG 4 Sorbitan monostearate), and TWEEN® 65 (PEG 20 Sorbitan tristearate). PLURONIC® surfactants are poly(ethylene oxide)-b-poly(propylene oxide)-b-poly(ethylene oxide) triblock copolymers. Commercially available PLURONIC® grades include PLURONIC® L121, PLURONIC® L122, PLURONIC® L123, PLURONIC® L122, PLURONIC® F127, PLURONIC® L101, PLURONIC® P103, PLURONIC® P104, PLURONIC® P105, PLURONIC® F108, PLURONIC® L121, PLURONIC® L122, PLURONIC® L123, PLURONIC® L122, PLURONIC® F127, PLURONIC® L92, PLURONIC® P94, PLURONIC® F98, PLURONIC® P81, PLURONIC® P84, PLURONIC® P85, PLURONIC® F87, PLURONIC® F86, PLURONIC® L72, PLURONIC® P75, PLURONIC® F77, PLURONIC® L61, PLURONIC® L62, PLURONIC® L63, PLURONIC® L64, PLURONIC® P65, PLURONIC® F63, PLURONIC® L42, PLURONIC® L43, PLURONIC® L44, PLURONIC® L31, PLURONIC® L35, and PLURONIC® F38.

In some embodiments, it is desirable to make particle 28 of a highly soluble material. Unaltered, such particles may dissolve too rapidly to embolize within a lumen at all. Others may dissolve too rapidly to embolize within a lumen long enough to effect a therapeutic response. Yet, the dissolution rate of such particles can be slowed to facilitate a suitable embolization period by techniques such as compression, mixing with less soluble compounds, or preparation of systems with entangled polymer chains.

Compression, which is often used in the pharmaceutical industry to make oral dosage forms, may be utilized to control dissolution of particles 28. A tablet press having cavities measuring 5-100 microns, may be used to exert high pressure, e.g., several tons per square inch, upon the materials of which particles 28 will be formed. This method of compression requires very small cavities, i.e., 5-100 microns, and even smaller precursor materials. Alternatively, a relatively large tablet may be formed by compression of materials from which particles 28 will be made. The tablet may then be broken into smaller pieces that would retain the compressed properties. Particles 28 of suitable size may then be obtained by sieving or by use of a centrifugal separator.

In an alternative compression method, particles 28 of a size near to the desired size are made using, for example, one of the above-described techniques. These particles 28 are blended with a compression material, such as a fatty acid or a wax. The compression material is soluble in a solvent in which the desired particles 28 are not soluble such as, for example, an aliphatic solvent. The compression material should be immiscible with particles 28. The blend of compression material and particles 28 is compressed at high pressure to form a block. The desired particles 28, now isotropically compressed, can be recovered by dissolving away the surrounding compression material using the solvent.

The mixing of highly soluble compounds with less soluble compounds to form particles 28 having a desired dissolution rate is another method of dissolution control. For example, the dissolution rate of microparticles made of galactose, a highly soluble compound, may be decreased by the addition of a small amount of a hydrophobic substance to the galactose. Such microparticles are marketed as ECHOVIST® and LEVOVIST®. ECHOVIST is a registered trademark of Schering of Berlin, Germany, and LEVOVIST is a registered trademark of Berlex Laboratories, Inc. of New Jersey. These particles are used as echocontrast media and are approved for intravenous use. The hydrophobic compounds in such particles may be replaced by hydrophobic therapeutic substances using methods known to those having ordinary skill in the art.

The addition of hydrophobic counterions to a selected polyelectrolyte polymer is another strategy for controlling the dissolution of particles 28 made thereof. The dissolution rate of water soluble heparin, for example, can be slowed by the addition of hydrophobic counterions. Such a complex is marketed under the tradename DURAFLO by Edwards Lifesciences Corporation of Irvine, Calif., a spin-off of Baxter International, Inc., of Deerfield, Ill. In addition, water soluble polymers such as carboxymethylcellulose and alginates can be made very water insoluble by employing calcium, magnesium, or barium as a counterion.

Dissolution control can also be achieved by selecting a very high molecular weight polymer, such as polyethylene oxide or polyvinylpyrrolidone, from which to make particles 28. Although water soluble, such materials dissolve slowly due to a high degree of polymer entanglement.

c. Neutralization

Certain polyelectrolytes are insoluble until neutralized. Polyacrylic acid as well as copolymers of acrylic acid with ethylene dissolve slowly, since such compounds are gradually neutralized following introduction to the bloodstream. The rate of neutralization, and thus the rate of dissolution, can be controlled by varying the molecular weight and/or the composition of the copolymer or by using an already partially neutralized polyelectrolyte in the preparation of particle 28.

d. Rapid Disintegration

As an alternative to complete dissolution, rapid disintegration of particles 28 into fragments that are small enough not to embolize a vessel, i.e., less than 5 microns, can be used to facilitate embolization for a suitable transitory period. In addition, rapid disintegration of particles 28 can be used to ensure that embolization does not occur until the small fragments have traveled sufficiently downstream from the location of delivery of particles 28. Such disintegration can be accomplished by incorporating very hygroscopic substances into particles 28. Examples of such disintegrants include, but are not limited to, croscarmellose and povidone, both of which are used as "super-disintegrants" in oral tablets. In addition, both of these compounds have been used in parenteral formulations. Disintegrants can be incorporated in a single core, in multiple cores, or as a complete dispersion in particle 28. Such methods of incorporation of disintegrants are well known by those having ordinary skill in the art. The disintegrant-containing particles 28 absorb large amounts of water, swell, and finally disintegrate.

Use of rapid disintegration as the method of limiting the time of embolization, or alternatively as the method of controlling the location at which embolization will occur, allows much flexibility in selecting the material from which to make particles 28. As long as the fragments of particles 28 are small enough to prevent further embolization, or alternatively to sufficiently delay embolization, the material of which particles 28 are made can have a slower dissolution rate than would be suitable in the absence of such disintegrants within particles 28.

Control of Platelet Attachment and Coagulation

It will be apparent to those of ordinary skill in the art that platelet attachment and coagulation may result upon the embolization of particle 28. In some instances, particle 28 may effectively clean itself by shedding proteins and platelets during dissolution. In other instances, the dissolution rate of particle 28 may be slowed by the barrier created by such proteins and platelets. In addition, platelet attachment and coagulation may lead to undesirable thrombosis of the embolized vessel.

One method of controlling platelet attachment and coagulation is to incorporate a material having anti-coagulant or anti-thrombogenic properties into particle 28. By example and not limitation, 1-30% by weight heparin may be included in particle 28.

Another method of controlling platelet attachment and coagulation is to incorporate a material having anti-coagulant or anti-thrombogenic properties into the infusion solution utilized to deliver particles 28 to the treatment site. By example and not limitation, 10-100 USP units of heparin per milliliter of infusion solution may be employed.

Use of the Composition

Suitable Anatomical Structures

Particle 28 is capable of being delivered to anatomical structure 10. Anatomical structure 10 can be any portion of a network of lumens, or of an individual lumen, capable of carrying a substance or a fluid in the mammalian anatomy. The configuration of anatomical structure 10 is not limited to the configuration illustrated by the Figures.

Figure 3A:
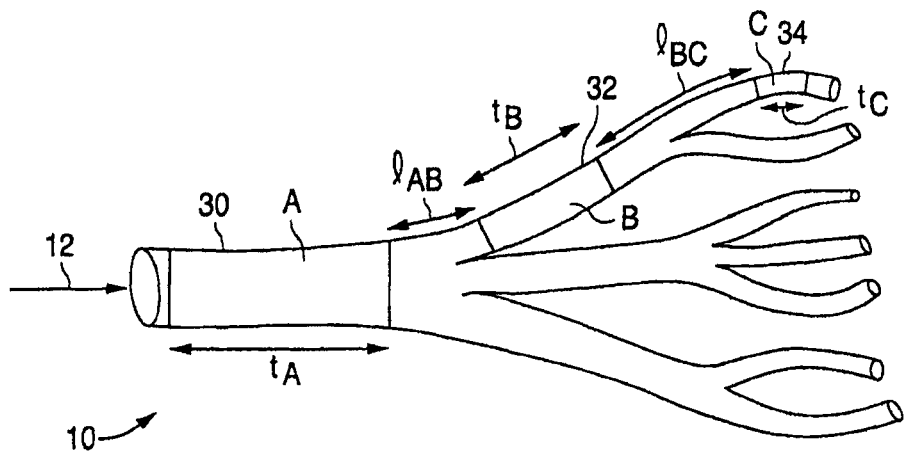
FIG. 3A illustrates an anatomical structure having a selected network of lumens in accordance with one embodiment of the present invention.

The number of lumens within anatomical structure 10 is not of critical importance. Anatomical structure 10 may be a lumen network having any number of lumens branching off in the downstream direction 12 into any number of other lumens, as depicted in FIG. 3A. In general, the lumens within a lumen network become progressively smaller in the downstream direction 12. The cross-sectional diameter of an individual lumen within the lumen network can be generally constant throughout. Typically, however, an individual lumen has a variable cross-sectional diameter. Regardless of the number of lumens within the lumen network and the relative sizes thereof, anatomical structure 10 in the form of a lumen network contains at least one region of smaller diameter located downstream from a region of larger diameter. The lumen network of FIG. 3A includes a first region 30, a second region 32 located downstream from first region 30, and a third region 34 located downstream from second region 32.

Figure 3B:
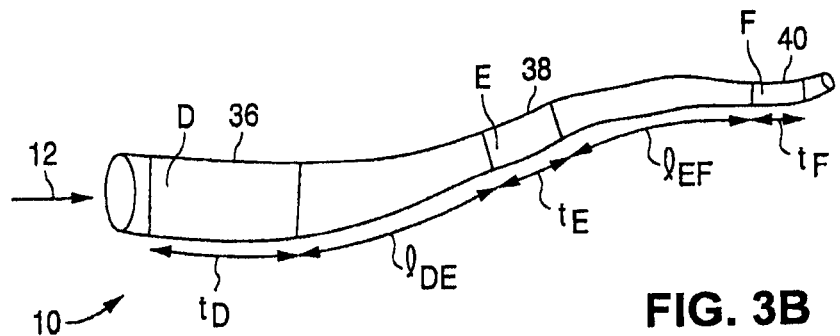
FIG. 3B illustrates an anatomical structure having a single lumen in accordance with another embodiment of the present invention.

Alternatively, anatomical structure 10 may include a single lumen, as depicted in FIG. 3B. In such embodiments, the cross-sectional diameter of the lumen can be generally constant throughout the conduit so long as the lumen contains at least one region of smaller diameter located downstream from a region of larger diameter. The lumen of FIG. 3B includes a first region 36, a second region 38 located downstream from first region 36, and a third region 40 located downstream from second region 38.

Hereinafter, the term "first region" will be used to refer to the region furthest upstream and having the largest cross-sectional diameter, and the term "second region" will be used to refer to the region downstream of the first region and having a cross-sectional diameter smaller than that of the first region. In embodiments containing a third region, the term "third region" will be used to refer to the region downstream of the second region and having a cross-sectional diameter smaller than that of the second region.

The term "region" is broadly defined to include a cross-sectional area, for example areas A, B, or C of FIG. 3A and areas D, E, or F of FIG. 3B, having any given thickness, for example, thickness $t_A$, $t_B$, or $t_C$ of FIG. 3A and thickness $t_D$, $t_E$ or $t_F$ of FIG. 3B. The distance between regions within anatomical structure 10 can be of any given length, for example length $l_{AB}$ or $l_{BC}$ in FIG. 3A and length $l_{DE}$ or $l_{EF}$ in FIG. 3B. Further, in embodiments in which anatomical structure 10 is a lumen network, such as that depicted in FIG. 3A, multiple regions may be located in the same lumen or in different lumens within the lumen network.

A particularly useful site of delivery of particle 28 is within the cardiovascular system of a mammalian subject. Thus, although the present disclosure is equally applicable to other anatomical structures 10 within a mammalian subject, the following description and accompanying Figures will detail the use of novel compositions and methods within the mammalian cardiovascular system, and more particularly within the mammalian arterial system.

Delivery of the Composition

Particle 28 is delivered to a predetermined site within anatomical structure 10. In general, particle 28 is delivered to the upstream, larger region within anatomical structure 10 having at least two regions as defined above. More particularly, in embodiments where anatomical structure 10 is a lumen network, such as that depicted in FIG. 3A, particle 28 is delivered to first region 30. Similarly, in embodiments where anatomical structure 10 is a single lumen, such as that depicted in FIG. 3B, particle 28 is delivered to first region 36. In addition, in embodiments in which a lumen within anatomical structure 10 is partially or totally occluded, particle 28 should be delivered at a location upstream of the occlusion.

Figure 4A:
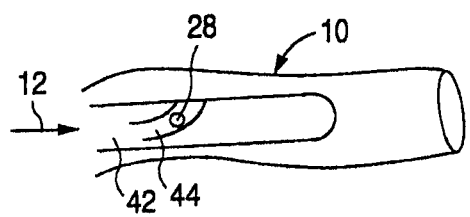
FIGS. 4A and 4B illustrate acts performed in accordance with one method of delivering the composition to an anatomical structure.
Figure 4B:
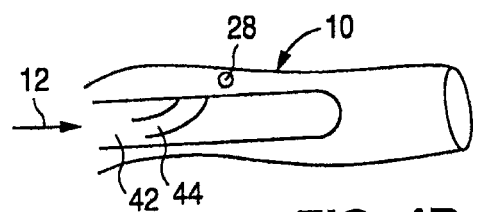

The particular method of delivery of particle 28 is not of critical importance so long as the method chosen facilitates delivery to a predetermined site of anatomical structure 10 as described above. One possible method of delivery utilizes catheter 42 equipped with a delivery lumen 44 containing particle 28 as illustrated in FIG. 4A. This method of delivery is suitable for use whether anatomical structure 10 is a lumen network or a single lumen. Catheter 42 is advanced into anatomical structure 10 until delivery lumen 44 is positioned at the location at which particle 28 is to be released. Once in position, particle 28 is released from delivery lumen 44 of catheter 42 into anatomical structure 10, as depicted in FIG. 4B. In some embodiments, catheter 42 is attached to a programmable pump which may be worn internally or externally. In such embodiments, the pump is programmed to deliver pulses of particles 28 at a preselected interval ranging from several hours to several days.

Figure 5A:
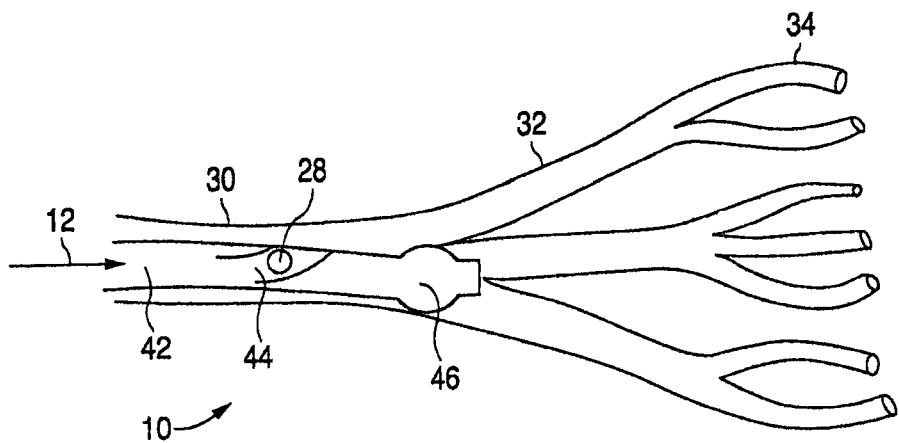
FIGS. 5A and 5B illustrate acts performed in accordance with one method of delivering the composition to a selected network of lumens.
Figure 5B:
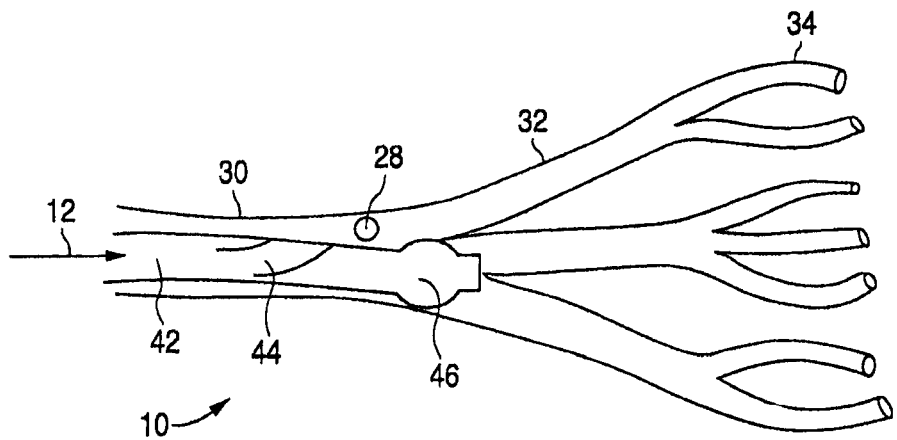

Yet another possible delivery method utilizes catheter 42 equipped with a single balloon 46 and a delivery lumen 44 containing particle 28 as illustrated in FIG. 5A. This method of delivery is suitable for use with embodiments in which anatomical structure 10 is a lumen network rather than a single lumen. Catheter 42 is advanced into anatomical structure 10 until single balloon 46 is positioned downstream of the location at which second region 32 branches off from first region 30. Once in position, single balloon 46 is inflated to cause an occlusion in first region 30. Particle 28 is released from delivery lumen 44 of catheter 42 into first region 30 upstream of the location at which second region 32 branches off from first region 30 as depicted in FIG. 5B.

Figure 6A:
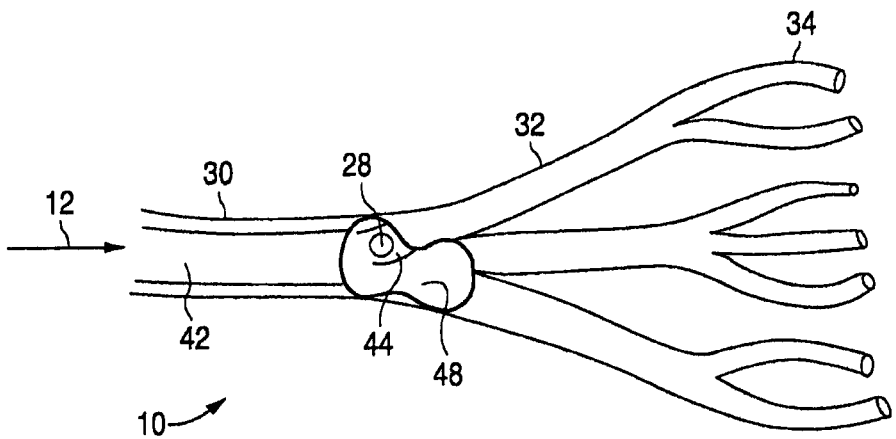
FIGS. 6A and 6B illustrate acts performed in accordance with another method of delivering the composition to a selected network of lumens.
Figure 6B:
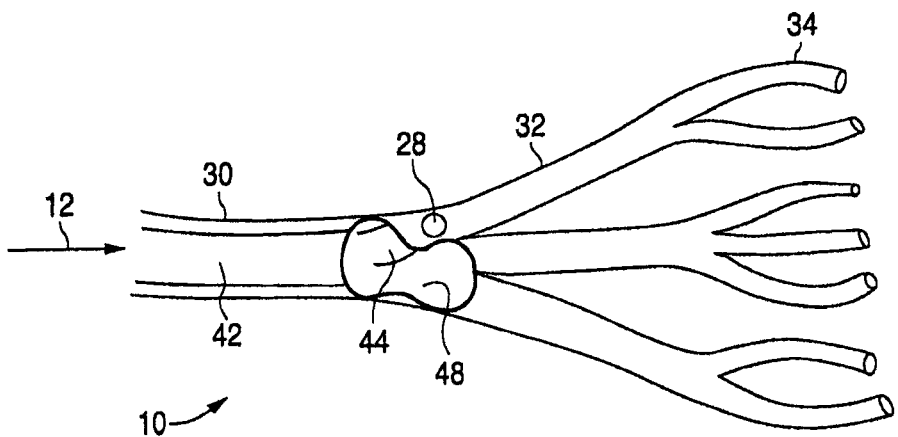

FIGS. 6A-6B illustrate another possible method of delivery suitable for use with embodiments in which anatomical structure 10 is a lumen network rather than a single lumen. Catheter 42 equipped with a double balloon 48 and a delivery lumen 44 containing particle 28, as illustrated in FIG. 6A. Catheter 42 is advanced into anatomical structure 10 until double balloon 48 is positioned to occlude the first region 30 at positions both upstream and downstream of the location at which second region 32 branches from first region 30. Double balloon 48 is inflated, occluding the anatomical structure 10, and particle 28 is released from delivery lumen 44 of catheter 42 into first region 30 between the occlusions as depicted in FIG. 6B.

Journey of the Composition within the Selected Anatomical Structure

Figure 7A:
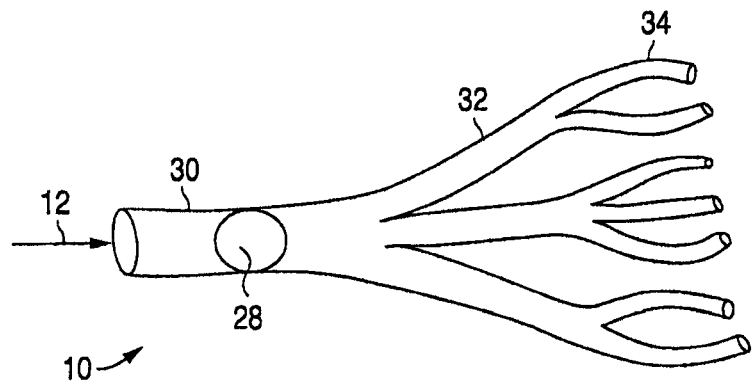
FIGS. 7A, 7B, and 7C illustrate use of the composition to induce a therapeutic response in an anatomical structure having a selected network of lumens in accordance with one embodiment of the present invention.
Figure 7B:
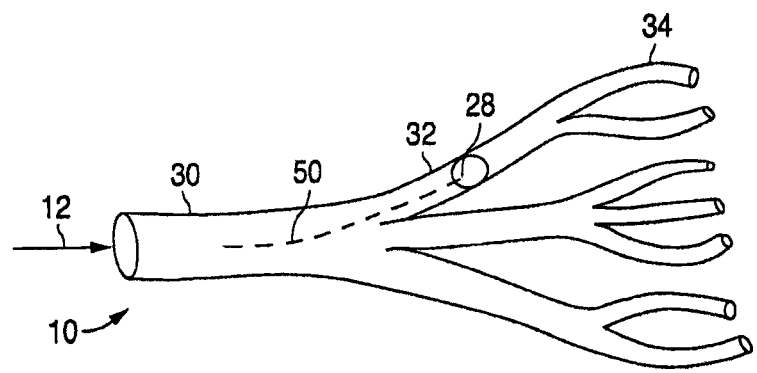
Figure 7C:
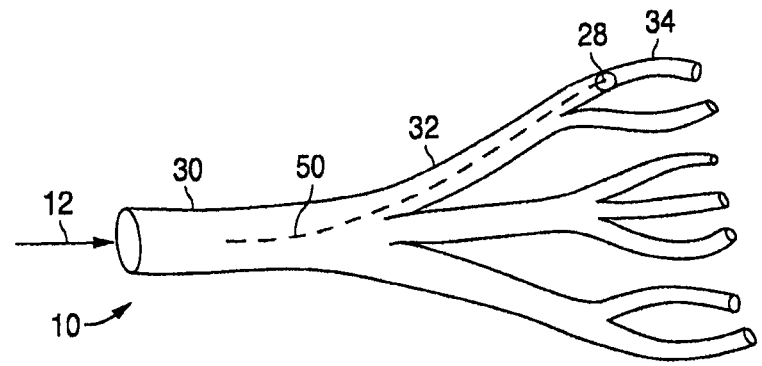

FIG. 7A depicts particle 28 upon delivery to first region 30 within anatomical network 10 in the form of a lumen network. Particle 28 has a first size too large to allow particle 28 to flow downstream from first region 30 to second region 32. Particle 28 is capable of size reduction such that particle 28 may reduce from its first size upon delivery to first region 30 to a smaller second size, allowing particle 28 to flow from first region 30 to the smaller second region 32 along path 50, as shown in FIG. 7B. In some embodiments, particle 28 must reduce from its second size to an even smaller third size to further flow along path 50 from second region 32 to third region 34, as shown in FIG. 7C.

Figure 8A:
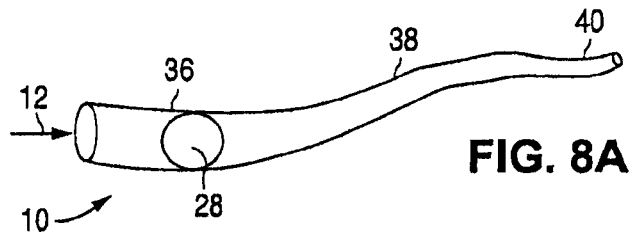
FIGS. 8A, 8B, and 8C illustrate use of the composition to induce a therapeutic response in an anatomical structure having a single lumen in accordance with another embodiment of the present invention.
Figure 8B:
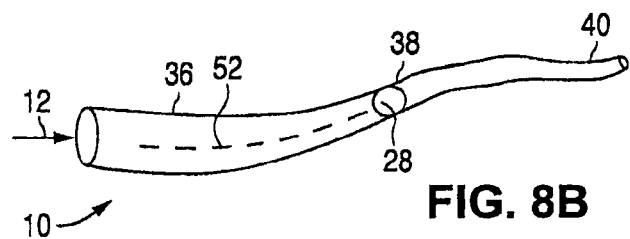
Figure 8C:
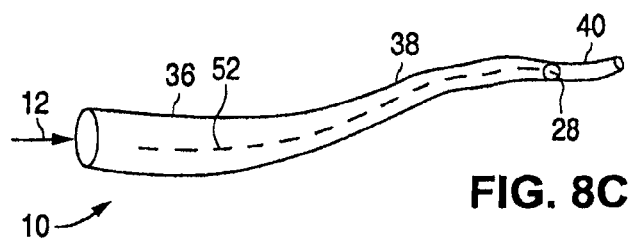

Similarly, FIGS. 8A-8C illustrate the journey of particle 28 along a path 52 within anatomical structure 10 in the form of a single lumen. Upon delivery to first region 36, as depicted in FIG. 8A, particle 28 has a first size too large to allow particle 28 to flow downstream from first region 36 to the smaller second region 38. Particle 28 is capable of size reduction such that particle 28 may reduce from its first size to a smaller second size, allowing particle 28 to flow from first region 36 to second region 38 along path 52, as shown in FIG. 8B. In some embodiments, particle 28 must reduce from its second size to an even smaller third size to further flow along path 52 from second region 38 to third region 40, as shown in FIG. 8C.

Figure 9A:
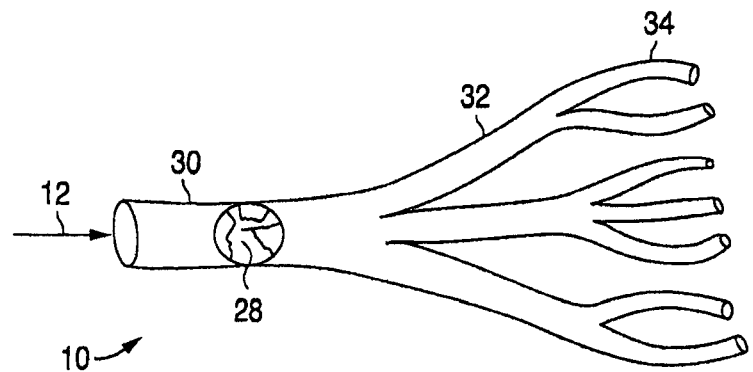
FIGS. 9A, 9B, and 9C illustrate use of the composition to induce a therapeutic response in an anatomical structure having a selected network of lumens in accordance with another embodiment of the present invention.
Figure 9B:
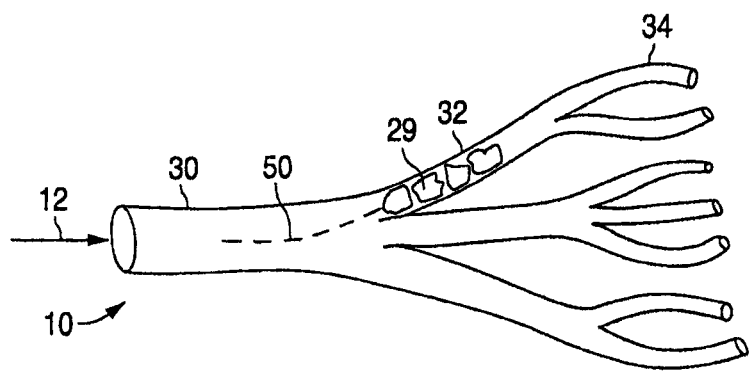
Figure 9C:
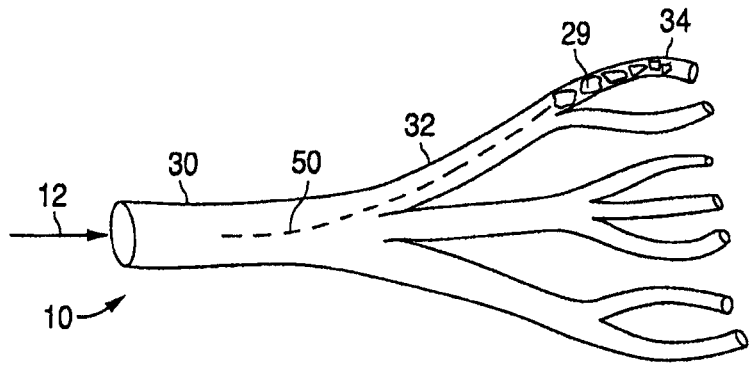

FIGS. 9A-9C illustrate an alternative embodiment in which particle 28 reduces in size by breaking into fragments 29 within anatomical network 10 in the form of a lumen network. Upon delivery to first region 30, as shown in FIG. 9A, particle 28 has a first size too large to allow particle 28 to flow downstream from first region 30 to second region 32. Particle 28 breaks into smaller fragments 29, allowing fragments 29 to flow from first region 30 to the smaller second region 32. Differences in the diameter of the branching lumens can permit the smaller fragments 29 to flow along path 50, as shown in FIG. 9B. In some embodiments, fragments 29 break into even smaller fragments 29 to further flow along path 50 from second region 32 to the smaller third region 34, as shown in FIG. 9C.

Figure 10A:
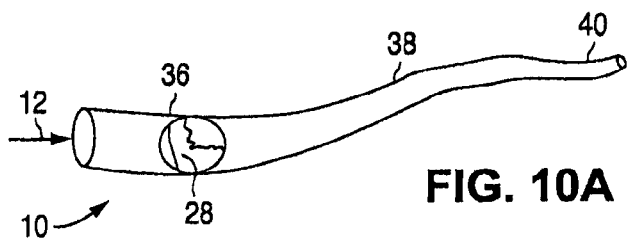
FIGS. 10A, 10B, and 10C illustrate use of the composition to induce a therapeutic response in an anatomical structure having a single lumen in accordance with another embodiment of the present invention.
Figure 10B:
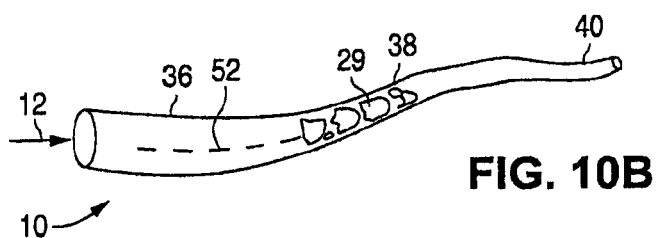
Figure 10C:
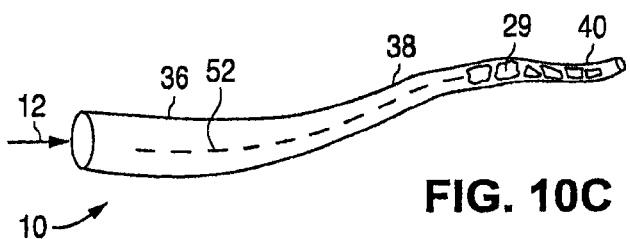

Similarly, FIGS. 10A-10C illustrate the route of particle 28 and fragments 29 thereof along a path 52 within anatomical structure 10 in the form of a single lumen. As depicted in FIG. 10A, particle 28 has a first size too large to allow particle 28 to flow downstream from first region 36 to second region 38 upon delivery to first region 36. In FIG. 10B, particle 28 breaks into smaller fragments 29, allowing fragments 29 to flow from the larger first region 36 to the smaller second region 38 along path 52. In some embodiments, fragments 29 must break into even smaller fragments 29 to further flow along path 52 flow from second region 38 to third region 40, as shown in FIG. 10C.

Therapeutic Effects Achieved Via Use of the Composition

In some embodiments, a therapeutic substance is released from particle 28 or fragments 29 thereof. In some embodiments, a therapeutic substance is released from particle 28 as particle 28 reduces in size and passes along path 50 or path 52 within anatomical structure 10, as shown in FIG. 7A-7C or 8A-8C, respectively. Similarly, in embodiments in which particle 28 breaks into fragments 29, a therapeutic substance is released from fragments 29 as fragments 29 break into smaller fragments 29, or otherwise reduce in size, and pass along path 50 or path 52, as shown in FIGS. 9A-9C and 10A-10C, respectively. In each of the above-described embodiments, particle 28 or fragments 29 thereof reduce in size at a rate such that particle 28 or fragments 29 do not embolize within anatomical structure 10 but rather flow unhindered through anatomical structure 10. Such embodiments facilitate local delivery of a therapeutic substance within anatomical structure 10 for the treatment of a patient.

In alternative embodiments, a therapeutic substance is released into anatomical structure 10 by a temporarily stationary particle 28 or at least one fragment 29 thereof. Upon reaching a lumen diameter through which it cannot pass while traveling along path 50 or path 52 of FIG. 7B-7C or 8B-8C, respectively, particle 28 will become constrained at that location in anatomical structure 10, thus embolizing within the lumen. Similarly, upon reaching a lumen diameter through which it cannot pass while traveling along path 50 or path 52 of FIG. 9B-9C or 10B-10C, respectively, at least one fragment 29 of particle 28 will become constrained at that location in anatomical structure 10, thus embolizing within the lumen. The therapeutic effect, however, is not achieved via cell damage or cell death, as embolization will continue only until particle 28 or fragment 29 sufficiently reduces in size to continue flowing through anatomical structure 10. Rather, the therapeutic effect is achieved via sustained release of the therapeutic substance from particle 28 or fragment 29.

The duration of the transitory period of embolization is typically less than one week. The exact duration will vary depending on the size of the vessel as well as on its location in the body. For example, a suitable embolization period for vessels within the brain is measured in seconds, and a suitable embolization period for vessels within the coronary system may be several minutes. The prolonged residence time of particle 28 or fragment 29 at the location of embolization yields a prolonged residence time of the released therapeutic substance at the location of embolization as well. In addition, since blood flow is temporarily halted at the location of embolization, the therapeutic substance is not immediately washed away from the vessel wall. Further, in some embodiments, the therapeutic substance may be released along path 50 or path 52 before and/or after the transitory period of embolization in addition to the above-described release of the therapeutic substance during the transitory period of embolization.

In still other embodiments, a therapeutic bodily response is not induced by the release of a therapeutic substance from particle 28 nor from fragments 29 thereof. Rather, particle 28 or fragments 29 effect a therapeutic bodily response within anatomical structure 10. The therapeutic bodily response, however, is not achieved via cell damage or cell death but via a transitory period of embolization while the therapeutic substance is gradually released and applied according to the relative sizes of the fragments and lumens. Following the delivery of particle 28 having a first size to anatomical structure 10, particle 28 travels along path 50 of FIGS. 7B-7C or path 52 of FIGS. 8B-8C until reaching a lumen diameter through which particle 28 cannot pass. Particle 30 remains at that location in anatomical structure 10, thus embolizing within the vessel, until particle 28 sufficiently reduces from the first size to a smaller second size, thereby causing a brief period of reduced blood flow. Similarly, following the delivery of particle 28 having a first size to anatomical lumen 10, particle 28 breaks into fragments 29 that travel along path 50 of FIGS. 9B-9C or path 52 of FIGS. 10B-10C until reaching a lumen diameter through which a least one fragment 29 cannot pass. Fragment 29 remains at that location in anatomical structure 10, thus embolizing within the vessel, until fragment 29 sufficiently breaks into smaller fragments 29, or otherwise reduces in size, thereby causing a brief period of reduced blood flow. Whether caused by the embolization of particle 28 or of fragment 29, the resulting brief period of reduced blood flow induces a therapeutic bodily response within anatomical structure 10.

In one such embodiment, pulsed delivery of particles 28, as described above, may induce brief periods of reduced blood flow and thereby facilitate collateral growth. With each pulse, particle 28 will travel in the vasculature until reaching a diameter through which it cannot pass, thus embolizing the vessel and inducing local ischemia. The embolization of the vessel is temporary in nature, as particle 28 will reduce in size. Several brief periods of reduced blood flow may trigger a series of events leading to collateral growth in humans. Indeed, substantial collateral development has been induced in dogs after several weeks in which eight two-minute blood flow restrictions were caused every twenty-four hours. Although particle 28 may additionally release a therapeutic substance to the region at which the vessel is embolized to induce collateral growth of vasculature, temporal modulation of blood flow by embolization alone can effectively induce collateral growth without application of the therapeutic substance.

EXAMPLES

Exemplary embodiments of the invention are illustrated below. These examples are being given by way of illustration only and not by way of limitation. The parameters given are exemplary, not limiting.

Example 1

A solution of lecithin and dexamethasone is made by dissolving 15 grams of lecithine and 5 grams of dexamethasone in 100 ml of methylene chloride. A water-in-oil emulsion is prepared by stirring the solution with 250 ml of a solution of 0.5 perfluorotributylamine/PLURONIC®F68 in water with 1% (w/v) of heparin.

The emulsion is warmed to 40° C. to drive off the methylene chloride, forming microparticles. The microparticles are collected by filtration and washed with near-freezing water. Particles are dried overnight under vacuum at 50° C.

The particles may be separated by size using standard particle sizing equipment such as a cyclone or tangential flow filtration, as are well known by those having ordinary skill in the art. A most suitable size fraction has a range from about 10 microns to approximately 50 microns. Other particle sizes are possible.

Example 2

A solution of Basic Fibroblast Growth Factor (0.25 gram), heparin (1.0 gram), and lactose (2.5 gram) in phosphate buffer pH 7.4 (100 ml) with Human serum albumin (0.25 gram) is prepared, and emulsified in 250 ml of methylene chloride containing 1.75 grams of polylactide-co-glycolide. The resulting emulsion in quantity 100 ml is added to 500 ml water with 0.5% perfluorotributylamine/pluronic F-68, and a double emulsion of water-in-oil-in water is prepared.

The methylene chloride is removed by warming the double emulsion to 40° C. for two hours. The particles are filtered off, washed with water, mixed with an aqueous solution of mannose in potassium phosphate buffer (20% mannose, w/v), and freeze-dried according to standard methods.

The particles may be separated by size using standard particle sizing equipment such as a cyclone or tangential flow filtration, as are well known by those having ordinary skill in the art. A most suitable size fraction has a range from about 10 microns to approximately 50 microns. Other particle sizes are possible.

Example 3

A solution of plasmid DNA form gene construct (0.1 gram) and heparin (1 gram) is prepared by stirring the plasmid and the heparin in a solution of MW 100,000 dextran (5% w/v) and mannose (15% w/v) in water.

The solution is emulsified in 5.times. the volume cyclooctane with 0.5% SPAN 80.

The solution is filled into standard lyophilization vials and freeze-dried using standard industrial equipment and protocols.

The particles may be separated by size using standard particle sizing equipment such as a cyclone or tangential flow filtration, as are well known by those having ordinary skill in the art. A most suitable size fraction has a range from about 10 microns to approximately 50 microns. Other particle sizes are possible.

For administration of the particles produced using the foregoing procedures and other examples of procedures that would be known to one having ordinary skill in the art in combination with the disclosure herein, the particles are suspended in phosphate buffered saline with 0.5% perfluorotributylamine/PLURONIC® F68 and 10 IU units of heparin per ml. The suspension is suitably prepared immediately before use.

The particles can be locally infused using methods described hereinbefore.

Particle sizes, polymer types, and drug types are selected based on the treatment goal and intended procedure outcome. For example, if an angiogenic response in a particular set of vessels in the goal, then a DNA plasmid-promoting expression of VEGF is most suitable. The procedure outcome is the growth of numerous small blood vessels in the treated area.

Fibroblast Growth Factor (FGF) containing particles can be used to induce arteriogenesis, a process that enlarges existing small arteries. Particles are infused upstream of the treatment area, temporarily embolizing the downstream target area, and releasing the drug before disintegrating. The outcome is to boost growth among smaller arteries.

Dexamethasone particles can be used to deliver a drug to an area under conditions that inflammation should be suppressed.

While particular embodiments of the present invention have been shown and described, it will be obvious to those having ordinary skill in the art that changes and modifications can be made without departing from this invention in its broader aspects. For example, the mammalian lymphatic system comprises a heavily-branched network of lymphatic vessels. Accordingly, the present invention may be utilized for the localized delivery of a therapeutic substance to a lumen network, or an individual lumen, within the mammalian lymphatic system. Therefore, the appended claims are to encompass within their scope all such changes and modifications as fall within the true spirit and scope of this invention.

We claim:

1. A composition to form an embolus within a vascular lumen, the composition comprising a solid particle comprising a hydrophobic solid, a surfactant and a therapeutic substance; wherein the particle forms the embolus within the vascular lumen for a transitory period of less than one week;
   wherein the hydrophobic solid is a solid triglyceride, cholesterol, or a combination thereof; and
   wherein the surfactant is selected from the group consisting of sorbitan esters, polyethoxylated sorbitan esters, poly(ethylene oxide)-b-poly(propylene oxide)-b-poly(ethylene oxide) triblock copolymers, and combinations thereof.

2. The composition of claim 1, wherein the surfactant comprises a sorbitan ester.

3. The composition of claim 1, wherein the therapeutic substance is selected from the group consisting of antineoplastic, antiplatelet, anticoagulant, fibrinolytic, antimitotic, thrombin inhibitor, anti-inflammatory, antiproliferative, antioxidant, antiangiogenic, angiogenic, arteriogenic and anti-allergic substances, and combinations thereof.

4. The composition of claim 1, wherein the surfactant comprises a polyethoxylated sorbitan ester.

5. The composition of claim 1, wherein the surfactant comprises a poly(ethylene oxide)-b-poly(propylene oxide)-b-poly(ethylene oxide) triblock copolymer.

6. The composition of claim 1, wherein the hydrophobic solid is cholesterol.

7. The composition of claim 1, wherein the hydrophobic solid is a solid triglyceride.

8. The composition of claim 1, wherein the particle further comprises a disintegrant.

9. The composition of claim 8, wherein the disintegrant is croscarmellose.

10. The composition of claim 8, wherein the disintegrant is povidone.

11. The composition of claim 8, wherein the disintegrant is lactose.

12. The composition of claim 8, wherein the disintegrant is mannose.

13. The composition of claim 1, wherein the diameter of the particle is reduced within the vascular lumen or the particle disintegrates into fragments with the vascular lumen.

14. The composition of claim 8, wherein the diameter of the particle is reduced within the vascular lumen or the particle disintegrates into fragments within the vascular lumen.

* * * * *